(12) United States Patent
Tuereli et al.

(10) Patent No.: US 9,585,842 B2
(45) Date of Patent: Mar. 7, 2017

(54) SUSTAINED RELEASE GUANFACINE HCL FORMULATION

(71) Applicant: SALMON PHARMA GMBH, Basel (CH)

(72) Inventors: Akif Emre Tuereli, Saarlouis (DE); Bernd Baumstuemmler, Saarlouis (DE); Richard Ammer, Iserlohn (DE)

(73) Assignee: SALMON PHARMA GMBH, Basel (CH)

( * ) Notice: Subject to any disclaimer, the term of this patent is extended or adjusted under 35 U.S.C. 154(b) by 0 days.

(21) Appl. No.: 14/888,054

(22) PCT Filed: Apr. 28, 2014

(86) PCT No.: PCT/EP2014/058608
§ 371 (c)(1),
(2) Date: Oct. 29, 2015

(87) PCT Pub. No.: WO2014/174119
PCT Pub. Date: Oct. 30, 2014

(65) Prior Publication Data
US 2016/0058708 A1    Mar. 3, 2016

(30) Foreign Application Priority Data
Apr. 26, 2013   (EP) .................................... 13165512

(51) Int. Cl.
*A61K 9/14*   (2006.01)
*A61K 9/16*   (2006.01)
(Continued)

(52) U.S. Cl.
CPC .......... *A61K 9/1635* (2013.01); *A61K 9/1694* (2013.01); *A61K 9/2054* (2013.01); *A61K 31/165* (2013.01); *A61K 31/185* (2013.01)

(58) Field of Classification Search
None
See application file for complete search history.

(56) References Cited

U.S. PATENT DOCUMENTS 5,854,290 A    12/1998  Arnsten et al.
6,287,599 B1 *  9/2001  Burnside .............. A61K 9/2009
                                                              424/468
(Continued)

FOREIGN PATENT DOCUMENTS

WO    WO 00/61275    10/2000

OTHER PUBLICATIONS

International Preliminary Report on Patentability (Chapter I of the Patent Cooperation Treaty) corresponding to PCA/EP2014/058608 dated Oct. 27, 2015.
(Continued)

*Primary Examiner* — Robert A Wax
*Assistant Examiner* — Melissa Mercier
(74) *Attorney, Agent, or Firm* — Jenkins, Wilson, Taylor & Hunt, P.A.

(57) ABSTRACT

The present invention is directed to a pharmaceutical composition comprising guanfacine or a salt thereof in nanoparticle form and at least one non-pH dependent sustained release agent. The present invention further is directed to a method of producing said nanoparticles and to nanoparticles obtained by this method.

26 Claims, 18 Drawing Sheets

(51) Int. Cl.
*A61K 9/20* (2006.01)
*A61K 31/165* (2006.01)
*A61K 31/185* (2006.01)

(56) References Cited

U.S. PATENT DOCUMENTS

| | | |
|---|---|---|
| 6,811,794 B2 | 11/2004 | Burnside et al. |
| 2003/0152622 A1 | 8/2003 | Louie-Helm et al. |
| 2011/0262496 A1* | 10/2011 | Desai .................. A61K 31/135 424/400 |

OTHER PUBLICATIONS

International Search Report corresponding to International Application No. PCT/EP2014/058608 dated May 28, 2014.

* cited by examiner

US 9,585,842 B2

SUSTAINED RELEASE GUANFACINE HCL FORMULATION

FIELD OF THE INVENTION

The present invention is directed to a pharmaceutical composition comprising guanfacine or a salt thereof in nanoparticle form and at least one non-pH dependent sustained release agent. The present invention further is directed to a method of producing said nanoparticles and to nanoparticles obtained by this method.

BACKGROUND OF THE INVENTION

Guanfacine hydrochloride has a pH dependent solubility, being more soluble at low pH values than higher pH values. The dissolution rate of the substance is directly related to the solubility of this substance in the given medium. In the case of basic drugs such as guanfacine HCl dissolution rate thus is higher at low pH values compared to higher pH values. In case of sustained or extended release formulation this characteristic of the API is not desired due to the fact that drug release rate will be higher at earlier parts of the gastrointestinal tract than later segments of the gastrointestinal tract where the pH is higher. This in vivo situation can clearly be observed with dissolution studies where drug release rate is higher in low pH medium, such as pH 1.2 HCl medium, than pH 6.8 Phosphate buffer.

In such cases sustained release can not be maintained since most of the API will be dissolved in stomach at a higher rate compared to the intestines resulting in peak plasma levels in very early stages of absorption which decreases as the formulation reaches to the intestines.

Different sustained release formulations of guanfacine HCl were previously described in U.S. Pat. Nos. 5,854,290; 6,287,599; 6,811,794 where pH dependent release of guanfacine was modified using a pH dependent polymer and an acid in the sustained release formulations. A pH dependent polymer was used to limit the dissolution from sustained release formulation whereas an acid was used to create a micro pH environment to improve the dissolution of guanfacine HCl in basic media. However, the dissolution in acidic media was still higher than the dissolution of sustained release tablets in basic media.

US 2011/0262496 relates to drug therapy formulations for reducing the side effects associated with a therapeutic. In some embodiments, US 2011/0262496 provides a reduction in sleep- and diet-related side effects associated with a therapeutic. The formulation may be in the form of a nanoparticle having a mean diameter of 100-500 nm. The nanoparticles are obtained by milling for several hours.

US 2003/0152622 is directed to an erodible, gastric-retentive drug dosage form for delivering a pharmacologically active agent to the stomach, duodenum, and upper small intestine of a patient, the dosage form comprising the pharmacologically active agent incorporated in a matrix of at least one biocompatible, hydrophilic polymer that (a) swells in the presence of water in gastric fluid such that the size of the dosage form is sufficiently increased to provide gastric retention in the stomach of a patient in whom the fed mode has been induced, (b) gradually erodes within the gastrointestinal tract over a determinable time period, and (c) releases the active agent throughout the determinable time period.

SUMMARY OF THE INVENTION

It is an object underlying the present invention to provide a pharmaceutical composition comprising guanfacine or a salt form which provides decreased dissolution of guanfacine or a salt form in acidic media (stomach), increased dissolution in basic media (intestine) and thus a more pH independent dissolution behaviour.

In the present invention, a pH independent dissolution of guanfacine was realized through nanoparticulate formulations containing guanfacine.

In a first aspect, the present invention provides a pharmaceutical composition comprising guanfacine or a salt thereof and at least one non pH-dependent sustained release agent, wherein guanfacine or a salt thereof is incorporated in nanoparticles having a size of from 70-1,000 nm and/or having a polydispersity index of ≤0.5.

According to the second aspect of the present invention, a method of producing nanoparticles containing guanfacine or a salt thereof is provided comprising the steps of:
  a) providing a fluid mixture of guanfacine or a salt thereof with a solvent; and a fluid non-solvent;
  b) precipitating nanoparticles containing guanfacine or a salt thereof by colliding fluid streams of the fluid mixture and the non-solvent; and
  c) isolating the nanoparticles as a nanoparticle suspension.

In a third aspect, the present invention provides nanoparticles obtainable by the above method.

In the present invention nanoparticles are used having a decreased particle size and increased surface area to volume ratio which alters some of the physicochemical and biological properties of those particles dramatically in comparison to their larger counterparts. Dissolution rate and solubility are increased as a result of increased surface area to volume ratio regardless of the pH value. These nanoparticles thus are suitable for oral administration of guanfacine HCl.

Furthermore, the present invention discloses methods for producing nanoparticles comprising guanfacine HCl while simultaneously stabilizing these either with one or more supplementary pharmaceutically approved excipients, additives or surface modificators, with a resulting particle size of up to about 1,000 nm with a polydispersity index ≤0.5. Nanoparticles of guanfacine HCl may be formulated as sustained release dosage forms by comprising at least one non pH-dependent sustained release agent.

In a particularly preferred aspect of the present invention, the guanfacine (or salt thereof) is present in complex form where the solubility of guanfacine in acidic media or in stomach is decreased due to this complexation. Furthermore, nanoparticles prepared from this complex increase the dissolution of guanfacine in basic media which corresponds to the intestinal conditions, therefore providing the desired release profile.

DETAILED DESCRIPTION OF THE INVENTION

Definitions

Figure 1:
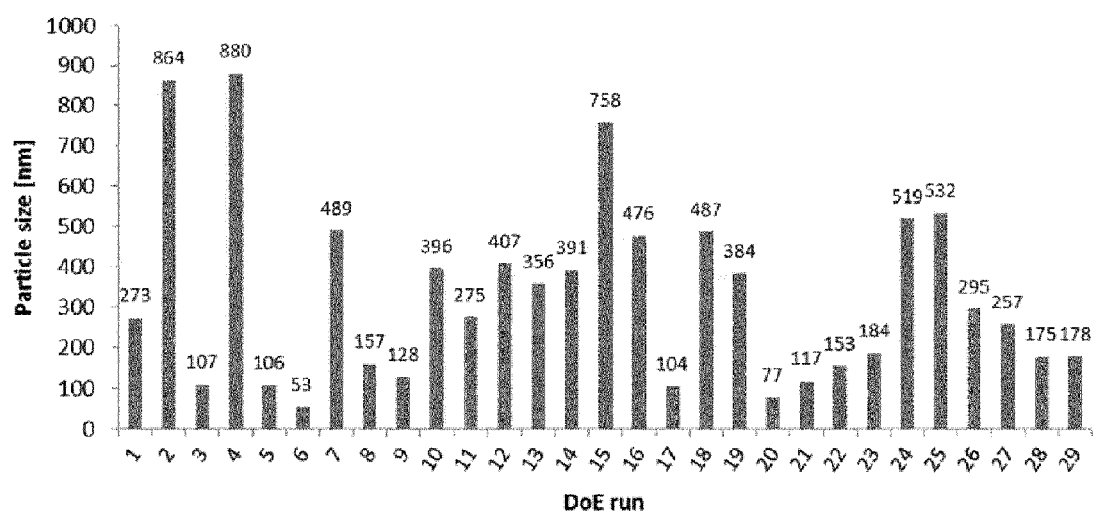
FIG. 1: Effect of nanoprecipitation process parameters temperature, pressure and flow rate on particle size (Visualization of Table 7)

Herein, the term "salt" means a "pharmaceutically acceptable salt" referring to derivatives of the disclosed compounds wherein the parent compound is modified by making salts thereof. For example, such conventional salts include, but are not limited to, those derived from inorganic acids such as hydrochloric, hydrobromic, sulfuric, sulfamic, phosphoric, nitric acid to name a few. Guanfacine HCl is in particular preferred.

A "non pH-dependent" sustained release agent is one which allows a release of guanfacine or a salt thereof in a time-dependent manner, substantially independent from the pH of the environment. As used throughout this specification and the appended claims, the term "sustained release", as applied to drug formulations, has the meaning ascribed to them in "Remington, The Science and Practice of Pharmacy," 22nd Ed., Pharmaceutical Press, (2012). Sustained release drug systems include any drug delivery system which achieves the slow release of drug over an extended period of time, and include both prolonged and controlled release systems. If such a sustained release system is effective in maintaining substantially constant drug levels in the blood or target tissue, it is considered a controlled release drug delivery system. If, however, a drug delivery system is unsuccessful at achieving substantially constant blood or tissue drug levels, but nevertheless extends the duration of action of a drug over that achieved by conventional delivery, it is considered a prolonged release system.

The nanoparticles of the present invention are defined by their size of about 70 to about 1,000 nm thus falling in the category of "fine" nanoparticles according to standard definitions. Their size is defined as their diameter determined by suitable processes, e.g. using dynamic light scattering (e.g. using a Malvern Zetasizer).

The term "fluid mixture" as used herein denotes a mixture of guanfacine or a salt thereof and a solvent. A solvent here is any kind of fluid substance which is capable of dissolving the API.

Although the term "fluid" as used in the present specification includes liquids, gases and plasmas according to standard definition, it usually means a substance which is liquid a room temperature (21° C.).

The term "non-solvent" according to the present invention describes any fluid substance which is capable of precipitating guanfacine containing nanoparticles by colliding a fluid stream of it with a fluid stream of the fluid mixture. Therefore, a "non-solvent" in the meaning of the present invention should not be interpreted narrowly, for example as a substance in which guanfacine or a salt thereof is insoluble.

The "polydispersity index" (PDI) is a parameter to define the particle size distribution of nanoparticles obtained from dynamic light scattering (DSL) measurements. As mentioned above, the PDI might be measured using a Malvern Zetasizer according to the manufacturer's instructions. The smaller the PDI value is, the lower the degree of particle size distribution. Generally, polydispersity Index PDI is used as degree of particle size distribution. Thus, particles/particle suspensions may be generally divided into monodisperse and polydisperse entities. For monodisperse, e.g. homogenous suspensions/particles, a tight particle size distribution is given. For polydisperse suspensions/particles, particle sizes vary considerably. Particle size as well as PDI are important factors affecting the dissolution rate of particular substances, e.g. pharmaceutical active ingredients. Thus, comparison of dissolution of 2 nanoparticular populations of one API with comparable mean particle sizes but significantly differing PDI might result in significant change in dissolution behavior of those nanoparticles, with slower dissolution for the nanoparticles with higher PDI and faster dissolution for the nanoparticles with lower PDI. Thus, PDI might affect, beside particle size, quality of nanoparticular products.

All percentages used herein are weight percent unless otherwise indicated.

One core element of the present invention is the preparation of guanfacine nanoparticles. Nanoparticles of guanfacine are produced using different methodology but using the pH dependent solubility of guanfacine HCl.

Precipitation Approach 1

In the first approach guanfacine HCl with a concentration of 1-12 mg/mL, preferably between 4-8 mg/mL is dissolved in an organic solvent such as but not limited to methanol, ethanol or isopropanol in the presence of stabilizing agents such as but not limited to Plasdone K90, Plasdone S630, Plasdone K12, Plasdone K25, Carbopol 980, Pluronic F68, Brij 35, Chremophor A25 with a concentration of 0.1-20 mg/mL, preferably 0.1-0.6 mg/mL. The precipitation was realised against a basic solution such as but not limited to KOH or NaOH solutions with molarities between 0.001 to 0.5, preferably between 0.1 to 0.2. Furthermore stabilizing agents were also included in basic solution such as but not limited to Plasdone K90, Plasdone S630, Plasdone K12, Plasdone K25, Carbopol 980, Pluronic F68, Brij 35, Chremophor A25 with a concentration of 0.1-20 mg/mL, preferably 0.1-0.6 mg/mL.

Precipitation Approach 2

In the second approach guanfacine HCl with a concentration of 1-30 mg/mL, preferably between 15-25 mg/mL was dissolved in an acidic solution which is named as solvent such as but not limited to citric acid, acetic acid, formic acid, hydrochloric acid solution with a pH value of 1-3.5, preferably 2-3 in the presence of stabilizing agents such as but not limited to Plasdone K90, Plasdone S630, Plasdone K12, Plasdone K25, Carbopol 980, Pluronic F68, Brij 35, Chremophor A25 with a concentration of 0.1-50 mg/mL, preferably 30-40 mg/mL. The precipitation was realized against an acidic solution which is named as non-solvent such as but not limited to citric acid, acetic acid, formic acid, hydrochloric acid solution with a pH value of 1-3.5, preferably 2-3 in the presence of SDS with a concentration of 1-20 mg/mL, preferably 4-8 mg/mL.

Complex Formation Approach

As third and most preferred approach nanoparticles were prepared from a complex with a 2 step process. First the complex was formed resulting in microparticles of API and complexing agent. In a second step, these microparticles were redissolved in a suitable solvent and precipitated against a non-solvent as nanoparticles.

The complex is realized for example with precipitation of guanfacine HCl solution, which is named as solvent, in acidic media such as but not limited to citric acid, acetic acid, formic acid, hydrochloric acid solution with a pH value of 1-3.5, preferably 2-3 with a concentration of 15-120 mg/mL, preferably between 75-100 mg/mL without any stabilizing agents, against an acidic solution which is named as non-solvent such as but not limited to citric acid, acetic acid, formic acid, hydrochloric acid solution with a pH value of 1-3.5, preferably 2-3 in the presence of SDS with a concentration of 15-120 mg/mL, preferably 75-100 mg/mL without any stabilizing agents. The formed complex was filtrated and dried at 40° C. followed by a sieving process. In the second step, the microparticulate complex was dissolved in an organic solvent such as but not limited to methanol, ethanol or isopropanol with a concentration of 5-100 mg/mL, preferably 75-100 mg/mL and precipitated against an acidic solution such as but not limited to citric acid, acetic acid, formic acid, hydrochloric acid solution with a pH value of 1-3.5, preferably 2-3 thus obtaining stable nanoparticles.

In summary, the process for the manufacturing of the guanfacine nanoparticles according to the third approach comprises the steps of:
a) providing an acidic solution of guanfacine or a salt thereof;
b) providing a further acidic solution, containing a complex forming agent, as a "non-solvent";
c) precipitating and isolating a guanfacine complex from these solutions;
d) dissolving the complex in a suitable organic solvent thus forming an organic solution; and
e) precipitating nanoparticles from the organic solution and a further acidic solution as a "non-solvent".

The mole ratio of Guanfacine:complexing agent preferably is about 1:1. "About" means a range of ±20%.

The use of guanfacine HCl as a salt of guanfacine and of SDS as complexing agent is preferred.

The complex of guanfacine which is formed in the presence of the complexing agent such as SDS showed increased solubility in organic solvents enabling preparation of stable nanoparticle suspensions with high concentrations. Therefore, this process provides for a much higher production capacity of the manufacturing process compared to prior art approaches which use time and work consuming milling processes for preparing the nanoparticles.

As outlined above, the present invention, according to a first aspect, provides a pharmaceutical composition comprising guanfacine or a salt thereof and at least one non pH-dependent sustained release agent, wherein guanfacine or a salt thereof is incorporated in nanoparticles having a size of from 70-1,000 nm and/or having a polydispersity index of ≤0.5.

A preferred size range of the nanoparticles of the present invention is 100-500 nm.

It is an important requirement of the nanoparticles according to the invention that their polydispersity index is ≤0.5. This guarantees homogenous distribution and quality of the nanoparticles and ensures a reliable and predictable oral bioavailability.

In a preferred embodiment of the invention, the guanfacine salt is guanfacine HCl, preferably in complex form. The complex may be realised with any pharmaceutically acceptable negatively loaded surfactant and polymer or salts thereof. The complex preferably is provided with sodium dodecylsulfate (SDS) or sodium deoxycholate.

Furthermore such nanoparticles of guanfacine HCl are formulated to sustained release dosage forms using pH-independent sustained release polymers and other pharmaceutically accepted excipients such as bulking agents, glidants, lubricants, binding agents.

The pH independent sustained release polymers may be one or more of carbohydrate gums, polyuronic acid salts, cellulose ethers, acrylic acid polymers and mixtures thereof. The carbohydrate gums may be one or more of xanthan gum, tragacanth gum, gum karaya, guar gum, acacia, gellan and locust bean gum. The polyuronic acid salts may be one or more of sodium alginate, potassium alginate and ammonium alginate. The cellulose ethers may be one or more of ethylcellulose, hydroxypropyl methylcellulose (HPMC), hydroxypropyl cellulose and hydroxyethyl cellulose. The acrylic polymer may be one or both of polyacrylic polymer and carboxy vinyl polymer. Most preferred pH independent sustained release polymers are ethylcellulose and HPMC.

The sustained release polymer will be present in an amount from about 1 to about 60%, preferably from about 10 to about 40% by weight based on the overall weight of the dry nanoparticles.

Bulking agents include but are not limited to lactose, microcrystalline cellulose, wood cellulose, corn starch, modified corn starch, calcium phosphate, sugar, dextrose, mannitol, sorbitol or mixtures of two or more thereof. The bulking agent will be present in an amount from about 1% to about 90%, preferably from about 5 to about 85% by weight.

Anti-adherents, glidants or lubricants include but are not limited to talc, magnesium stearate, fumed silica (micronized), polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate. These agents will be present in an amount from about 1 to go %, preferably from about 5 to about 85% by weight.

Binders include but not limited to acacia, tragacanth, sucrose, gelatin, glucose, starches, celluloses, alginic acid and salts of alginic acid, magnesium aluminum silicate, PEG, guar gum, polysaccharide acids, bentonites, povidone.

These agents will be present in an amount of 0.5% to about 15%, more preferably 1% to about 10% by weight.

In a second aspect, the present invention comprises a method of producing nanoparticles containing guanfacine or a salt thereof comprising the steps of:
a) providing a fluid mixture of guanfacine or a salt thereof with a solvent; and a fluid non-solvent;
b) precipitating nanoparticles containing guanfacine or a salt thereof by colliding fluid streams of the fluid mixture and the non-solvent; and
c) isolating the nanoparticles as a nanoparticle suspension.

The final step of isolating the nanoparticles may involve evaporation of the solvent/non solvent, preferably under vacuum.

The methods of the present invention thus preferably include controlled solvent/non-solvent precipitation where solvent and non-solvent streams collide as impinging jets with a high velocity of more than 1 m/sec, where the Reynold number is higher than 500. The velocity, in one embodiment, may be higher than 50 m/sec as well. It is noted that the above indicated velocity is the velocity of each of the colliding streams, i.e. both, the fluid stream of the fluid mixture and the fluid stream of the non-solvent have this velocity.

The solvent and non-solvent preferably are sprayed through nozzles usually smaller than 1000 μm (for example smaller than 500 μmm or 300 μm) with pressures of more than 1 bar. Pressures of more than 10 bar and even more than 50 bar are suitable as well. The pressure may be regulated by pressure regulators.

The two streams collide in a reactor, where a very rapid mixing takes place. Mixing times usually are below 1 millisecond, preferably below 0.5 millisecond and even more preferably under 0.1 millisecond. The flow rates of solvent and non-solvent streams may reach more than 600 l/hour. Thus, the two impinging jets (or streams) collide in the reactor where precipitation takes place forming disc like structures depending on the reactor geometry.

The mixing time is adjusted as a derivative of the flow rate, the higher the flow rate, the lower the mixing time will be. The mixing is done in the molecular state. In the reactor, where the fluid streams collide, two plates are formed because of the parallel streams flowing against each other. Then, the diffusion process starts from solvent to non-solvent and at the end of this diffusion, the mixture is completed. This time period can be controlled with the flow rate and also the gas pressure. This kind of mixing preferably is obtained with a so called microjet reactor since its structure allows the collision of two streams in a free chamber under gas so that the particle size can be controlled.

The term "precipitation reactor" or "microjet reactor" includes all the geometries that are defined in patent EP 1 165 224 A1 (=WO 0061275 A2). The contents of this patent application are incorporated herein by reference. EP 1 165 224 A1 provides for a system for the initiation of chemical or physical processes including at least two liquid media to be injected by means of pumps, preferably high-pressure pumps, into a reactor chamber enclosed by a reactor housing and on to a shared collision point, each medium being injected through one nozzle. Through an opening in the reactor chamber a gas, an evaporating liquid, a cooling liquid or a cooling gas is introduced so as to maintain the gas atmosphere in the reactor interior, notably in the collision point of the liquid jets, and to cool the resulting products. The resulting products and excess gas are removed from the reactor housing via a further opening by positive pressure on the gas input side or negative pressure on the product and gas discharge side.

As mentioned above, there are several approaches for forming the nanoparticle comprising pharmaceutical formulation of the present invention:

In a first approach, the solvent (for dissolving guanfacine or a salt thereof) is selected from organic solvents such as, but not limited to, methanol, ethanol, t-butanol, acetone or mixtures thereof. Then, the non-solvent is selected from an aqueous alkaline solvent, preferably, but not limited to, aqueous NaOH or KOH solutions.

In a second approach, the solvent is an acidic aqueous solvent, i.e. an aqueous solution of, for example, citric acid, acetic acid, formic acid or hydrochloric acid, preferably citric acid. In this case, the non-solvent then is an acidic aqueous solvent as well, for example, citric acid, acetic acid, formic acid or hydrochloric acid, preferably citric acid.

In a third and preferred approach, guanfacine or a salt thereof is complexed prior to nanoparticle formation. This is done in line with the above explanations, i.e. in a 2-step process. In a first step, the complex is formed by precipitating an acidic solution of guanfacine (or a salt thereof) and a complexing agent such as SDS against a further acidic solution. The mole ratio of guanfacine to SDS preferably is about 1:1. Both acidic solutions may be an aqueous solution of, for example, citric acid, acetic acid, formic acid or hydrochloric acid, however, the use of citric acid is preferred.

The aqueous solution is usually between 1-5% by weight. The best results have been achieved at a concentration of about 2% by weight. The so formed complex is then isolated and further used in the second step. The second step includes dissolving the complex in an organic solvent such as, but not limited to, methanol, ethanol, isopropanol, or acetone and precipitating nanoparticles against an aqueous solution of, for example, citric acid, acetic acid, formic acid or hydrochloric acid.

The so formed nanoparticles then are further processed to the final pharmaceutical formulation. This in the first place involves mixing the nanoparticle suspension obtained with a binder solution in water and granulating them onto a non pH dependent polymer such as either ethyl cellulose and/or HPMC. Also one or more of the other excipients mentioned above, can be added here. The final granulates then may be processed to the final dosage form such as to capsules, tablets etc. according to standard methods of pharmaceutical technology. It is referred to the methods disclosed, for example, in "Remington, The Science and Practice of Pharmacy," 22nd Ed., Pharmaceutical Press, (2012). The nanoparticles thus can be designed to be used in a variety of different pharmaceutical compositions and formulations such as oral delivery as tablets capsules or suspensions, pulmonary and nasal delivery, topical delivery as emulsions, ointments and creams, and parenteral delivery as suspensions, microemulsions or as a depot. Oral delivery is most preferred.

In a further embodiment, the fluid mixtures of guanfacine or salts thereof with a solvent and/or the non-solvent contain one or more additional active pharmaceutical ingredients (API's) and/or pharmaceutically acceptable auxiliaries.

Preferably, the volume ratio of the liquids of the solvent and non-solvent is between 1:1 and 1:2.

The present application now is described in more detail by the following Examples. However, it is noted that the Examples are provided for illustrative purposes only and should not be construed to limit the scope of the invention in any way.

Example 1

Guanfacine HCl and Pluronic F68 were dissolved in MeOH with a concentration of 6 mg/mL and 0.4 mg/mL respectively and nanoprecipitated against 0.1 N KOH solution containing PVP. The obtained suspension was composed of nanoparticles trapped in polymer matrix of PVP with a particle size of greater than 1 µm and those microparticles were stable and monodispersed (PDI<0.250). In this case solvent and non-solvent were pumped with a flow rate of 50 mL/min at 35° C. and with an inert gas pressure of 0.2 bar. Obtained microparticles were filtrated and dried. HPLC based assay analysis have shown 99.6% guanfacine HCl content.

Example 2

In order to avoid the problems arising from the hydrophilic nature of guanfacine HCl, counter-ion method (complex formation) was employed. In the counter-ion method a monovalent drug substance forms a self-assembled complex with monovalent charged SDS.

During the optimization studies, concentrations of SDS and guanfacine HCl (2.5-120 mg/mL), type (HCl, acetic acid, citric acid, formic acid) and pH of acidic medium (pH 1.2-3.5) and presence of stabilizers (Plasdone K90, Plasdone S630, Plasdone K12, Plasdone K25, Carbopol 980, Pluronic F68, Brij 35, Chremophor A25) and flow rate (1-50 mL/min) were investigated.

When 6 mg/mL SDS was employed, the formed complex was successfully stabilized by using 40 mg/mL Plasdone K25 which was dissolved in 20 mg/mL guanfacine HCl containing 5 wt % citric acid solution. Stable nanoparticles are formed due to columbian forces. In order to prepare these nanoparticles flow rate of 50 mL/min was used for solvent and non-solvent at 35° C. with an inert gas pressure of 0.2 bar.

Example 3

As the last and most preferred approach nanoparticles were prepared from a complex with a 2-step process. Basically first a microparticular complex was formed. The microparticular complex was dried and redissolved in solvent and precipitated against a non-solvent as nanoparticles.

Optimization studies revealed that in the absence of stabilizers, the formed complex shows relatively lipophilic character and the complex was not soluble in water or at low pH values. These characteristics possessed by the guanfacine HCl:SDS complex were further investigated in order to optimize the nanoparticles prepared. Guanfacine HCl:SDS mole ratio, flow rate, temperature, medium pH and drying temperature were chosen as critical parameters. Effects of those independent parameters on complex formation yield (guanfacine HCl based) were investigated.

In the experiments below concentration of guanfacine HCl in solvent was adjusted to 10% which depends on the solubility of guanfacine in aqueous media with low pH.

Complex formations were carried out at different mole ratios of SDS and guanfacine HCl, in order to optimize the amount of SDS required to form a stable complex with guanfacine HCl. Complex formation was realized using a microjet reactor and the solvent/non-solvent system was delivered at equal flow rates of 50 mL/min. No nitrogen supply was used during the process and the temperature was adjusted to 35° C. Following preparation, the complex was filtrated and dried.

Among the experiments conducted at 0.5:1, 0.75:1:0, 1:1, 1:1.5 and 1:2 mole ratios, 1:1 guanfacine HCl:SDS ratio was determined as the most effective one. At lower ratios (0.5:1.0 and 0.75:1.0) cloudy complex formation was observed, however complex formation yields were low (39.2% and 68%, respectively). On the other hand, at higher ratios (<1:1.5 and 1:2) pearl like clumps of complex was formed and complex yield formations were low, as well (56.4% and 62.5%, respectively). Yield of complex formation was 98.2% when equivalent moles of guanfacine HCl and SDS were used (1:1), which is probably due to prevention of excess amounts of free drug substance or SDS.

TABLE 1

Effect of mole ratio of guanfacine HCl:SDS on complex formation

| | Ratio [mole:mole] | guanfacine HCl based Yield [%] |
|---|---|---|
| 1 | 0.5:1 | 39.2 |
| 2 | 0.75:1 | 68.0 |
| 3 | 1:1 | 98.2 |
| 4 | 1:1.5 | 56.4 |
| 5 | 1:2 | 62.5 |

Since guanfacine HCl shows pH dependent solubility characteristics, effect of pH on complex formation has been investigated. Equal concentrations (10%) of guanfacine HCl and SDS were dissolved in different concentrations of citric acid solutions and yield was compared. Complex formation was realized with a microjet reactor and solvent/non-solvent system was delivered at equal flow rates of 50 mL/min at 35° C. No nitrogen supply was used during the process. Following preparation, the complex was filtrated and dried. The obtained complexes were evaluated in means of complex yield. Although the yields did not differ drastically, and no degradation depending on the citric acid concentration was observed, 2% citric acid was chosen as working concentration, since best yields were obtained at that concentration.

TABLE 2

Effect of citric acid concentration (pH) on complex formation

| | Citric acid concentration [wt %] | guanfacine HCl based Yield [wt %] |
|---|---|---|
| 1 | 1% | 98.4 |
| 2 | 2% | 98.8 |
| 3 | 3% | 98.2 |
| 4 | 4% | 96.4 |
| 5 | 5% | 96.5 |

Effect of flow rate on complex formation was investigated, as well. Complex formation was realized with a MJR and equivalent concentrated solvent/non-solvent systems were delivered at equal flow rates (ranging between 5 and 50 mL/min) in order to ensure 1:1 mole ratio. No nitrogen supply was used during the process in order to prevent foam formation arising from pumping SDS solution at high flow rates. The temperature was adjusted to 35° C. Following preparation, the complex was filtrated and dried. Optimization studies have shown that flow rate being used to deliver the solvent/non-solvent system had no effect on complex properties or yield of complex formation as shown in Table 3.

TABLE 3

Effect of flow rate on complex formation

| | Solvent System Flow Rate [mL/min] | Non-Solvent System Flow Rate [mL/min] | guanfacine HCl based Yield [%] |
|---|---|---|---|
| 1 | 5.0 | 5.0 | 98.2 |
| 2 | 10.0 | 10.0 | 98.6 |
| 3 | 25.0 | 25.0 | 98.2 |
| 4 | 50.0 | 50.0 | 98.3 |

Effect of temperature on complex formation was investigated in a temperature range of 25-45° C. Complex formation was realized with MJR and equivalent concentrated solvent/non-solvent systems were delivered at 50 mL/min and no nitrogen gas was used, as previously defined. Studies have shown that system temperature had no effect on complex formation (Table 4). In order to prevent energy consumption and an additional heating step during complex preparation that would be required at elevated temperatures, system temperature is chosen as 25° C.

TABLE 4

Effect of temperature on complex formation

| | Temperature [° C.] | Solvent/Non-Solvent System Flow Rate [mL/min] | guanfacine HCl based Yield [%] |
|---|---|---|---|
| 1 | 25.0 | 50:50 | 98.6 |
| 2 | 30.0 | 50:50 | 98.1 |
| 3 | 35.0 | 50:50 | 98.4 |
| 4 | 40.0 | 50:50 | 98.2 |
| 5 | 45.0 | 50:50 | 97.9 |

Following complex formation, the complex is filtrated and dried. In order to observe the effect of drying temperature on complex quality after 24 hr of drying, a range of drying treatments at different temperatures was evaluated. The quality related properties were chosen as structural properties (particle size), optical properties (color, appearance) and degradation profile (total impurity %). Particle size was evaluated in means of dry complex sieving (sieve analysis). 1 g of complex was loaded into 1 μm sieve and shaken for 5 min. Amount of complex onto sieve (>1 μm) and in the collecting tray (<1 μm) were evaluated and results were expressed in %. Level of total impurity was determined with HPLC. Maximum allowed total impurity specification was set as <1%. Studies have shown that drying temperature has no effect on structural or optical properties and does not cause degradation of the product within the applied temperature interval as shown in Table 5.

TABLE 5

Effect of drying temperature on complex properties

| Drying Temperature [° C.] | Structural Properties | | Optical Properties | | Total Impurity [%] |
|---|---|---|---|---|---|
| | Particle size <1 μm [%] | Particle size >1 μm [%] | Color | Appearance | |
| 30.0 | 99.4 | 0.6 | White to off white | Porous powder | conforms |
| 35.0 | 99.2 | 0.8 | White to off white | Porous powder | conforms |
| 40.0 | 99.3 | 0.7 | White to off white | Porous powder | conforms |

Guanfacine HCl/SDS complex in dried microparticular form was dissolved in a suitable solvent and precipitated against a non-solvent in a second step in order to produce guanfacine HCl in nanoparticular form. Design of Experiment (DoE) was used in order to understand and control the production process. Flow rate, temperature and pressure were chosen as independent factors, particle size was assigned as dependent factor. For the DoE, go mg/mL guanfacine HCl equivalent complex dissolved in acetone was used as solvent system and pH 2.1 formic acid solution was used as non-solvent system and solvent/non-solvent ratio was assigned as 1:2 in accordance with prior findings. Non-solvent flow rate was assigned as twice of the solvent flow rate included in the design. Response surface study type with Box-Behnken initial design was chosen since it serves for finding ideal process settings and optimal performance. Design space for the optimization study is provided in Table 6, results are given in Table 7.

TABLE 6

Design space for the optimization study of nanoparticle production

| Factor | Type | Name | Unit | Low actual | Low coded | High Actual | High coded | Mean |
|---|---|---|---|---|---|---|---|---|
| A | numeric | Flow rate Solvent | mL/min | 5.0 | −1 | 25.0 | +1 | 15.0 |
| B | numeric | Temperature | ° C. | 25.0 | −1 | 60.0 | +1 | 42.5 |
| C | numeric | Pressure | bar | 0.1 | −1 | 2.0 | +1 | 1.0 |

TABLE 7

Summarized conditions and corresponding Design of Experiment results

| Run | Flow rate [mL/min] | Temperature [° C.] | Pressure [bar] | Particle size [nm] |
|---|---|---|---|---|
| 1 | 15.00 | 42.50 | 1.00 | 273.30 |
| 2 | 5.00 | 42.50 | 1.00 | 864.20 |
| 3 | 15.00 | 42.50 | 2.00 | 107.20 |
| 4 | 15.00 | 25.00 | 1.00 | 880.10 |
| 5 | 5.00 | 60.00 | 1.00 | 106.30 |
| 6 | 15.00 | 60.00 | 2.00 | 53.49 |
| 7 | 15.00 | 42.50 | 0.00 | 488.80 |
| 8 | 15.00 | 60.00 | 1.00 | 157.40 |
| 9 | 15.00 | 42.50 | 1.00 | 127.70 |
| 10 | 25.00 | 42.50 | 1.00 | 395.60 |
| 11 | 15.00 | 25.00 | 0.10 | 274.80 |
| 12 | 5.00 | 42.50 | 0.10 | 406.80 |
| 13 | 15.00 | 42.50 | 0.10 | 356.40 |
| 14 | 25.00 | 42.50 | 1.00 | 390.60 |
| 15 | 5.00 | 42.50 | 2.00 | 757.70 |
| 16 | 25.00 | 60.00 | 1.00 | 475.80 |
| 17 | 15.00 | 60.00 | 1.00 | 104.00 |
| 18 | 25.00 | 25.00 | 1.00 | 486.80 |
| 19 | 5.00 | 25.00 | 1.00 | 384.00 |
| 20 | 15.00 | 42.50 | 2.00 | 76.65 |
| 21 | 15.00 | 42.50 | 1.00 | 116.90 |
| 22 | 15.00 | 42.50 | 1.00 | 153.10 |
| 23 | 15.00 | 25.00 | 1.00 | 184.00 |
| 24 | 25.00 | 42.50 | 0.00 | 518.70 |
| 25 | 15.00 | 60.00 | 0.10 | 532.20 |
| 26 | 15.00 | 25.00 | 2.00 | 295.20 |
| 27 | 5.00 | 42.50 | 1.00 | 256.50 |
| 28 | 25.00 | 42.50 | 2.00 | 175.00 |
| 29 | 15.00 | 42.50 | 1.00 | 177.60 |

Figure 2:
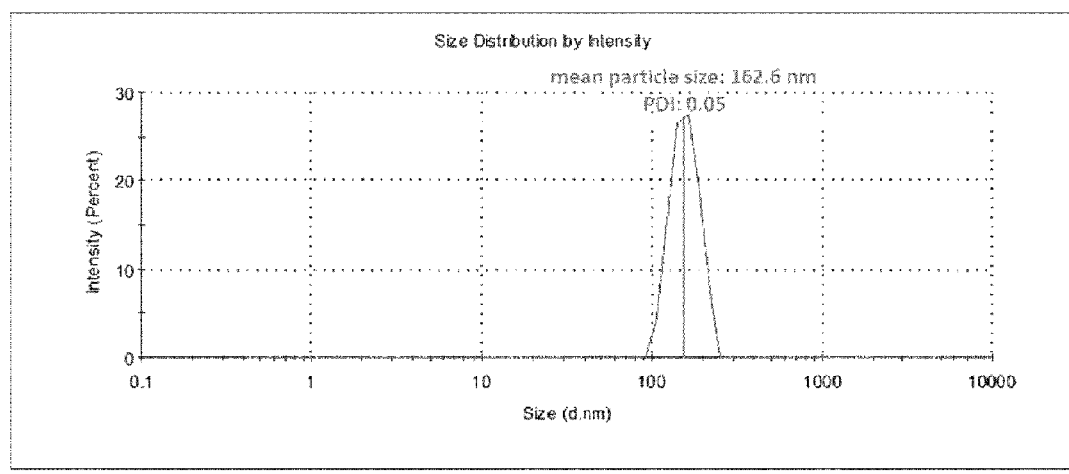
FIG. 2: Exemplary particle size measurement using a Malvern Particle sizer of guanfacine HCl nanoparticles produced with approach 3 (see below), displaying a mean particle size of 162.6 nm and a Polydispersity Index (PDI) of 0.05.

FIG. 1 shows Particle sizes of DoE runs 1 to 29. FIG. 2 shows exemplary particle size of guanfacine HCl nanoparticles produced with approach 3, displaying a mean particle size of 162.6 nm and a Polydispersity Index (PDI) of 0.05.

Example 4

Dissolution studies were conducted with different nanoparticle formulations described in Table 9 with the dissolution parameters described in Table 8.

TABLE 8

Dissolution testing parameters

| System | Erweka DT-6 |
|---|---|
| Apparatus | II (Paddle) |
| Speed [rpm] | 50 |
| Medium | Phosphate Buffer pH 6.8 + 0.5% Tween 80 |

TABLE 8-continued

| Dissolution testing parameters | |
|---|---|
| Volume [mL] | 500 |
| Medium Temperature [° C.] | 37.0 ± 0.5 |
| Sampling Times [min] | 5, 10, 20, 45, 60, 90 |

After reaching a temperature of 37±0.5° C. degrees, weighed amounts of nanoparticles were placed into each vessel which was performed by 60 seconds difference between each vessel. This time interval difference was taken into consideration during whole sampling. Temperature in the vessel 7 was controlled and documented for each sampling time point. 5 mL of sample was drawn from each vessel for each sampling point. Samples taken were filtrated using 1.0 µm glass syringe filters. The first 3 ml was transferred back into the vessel, while rest of the samples was transferred to a vial.

Samples were analyzed by employing validated HPLC method.

In case of formulation 3, formulation 4 and formulation 5 during the first step, guanfacine HCl is complexed by SDS both of which are dissolved in 2 wt % citric acid solutions. Problems arising from pH dependent solubility of guanfacine HCl were prevented with formation of these complexes. These complexes are collected from the medium by filtration and dried. In the second step the complex is dissolved in EtOH or acetone and nanoprecipitated against 2 wt % citric acid or pH 2.1 formic acid.

Figure 3:
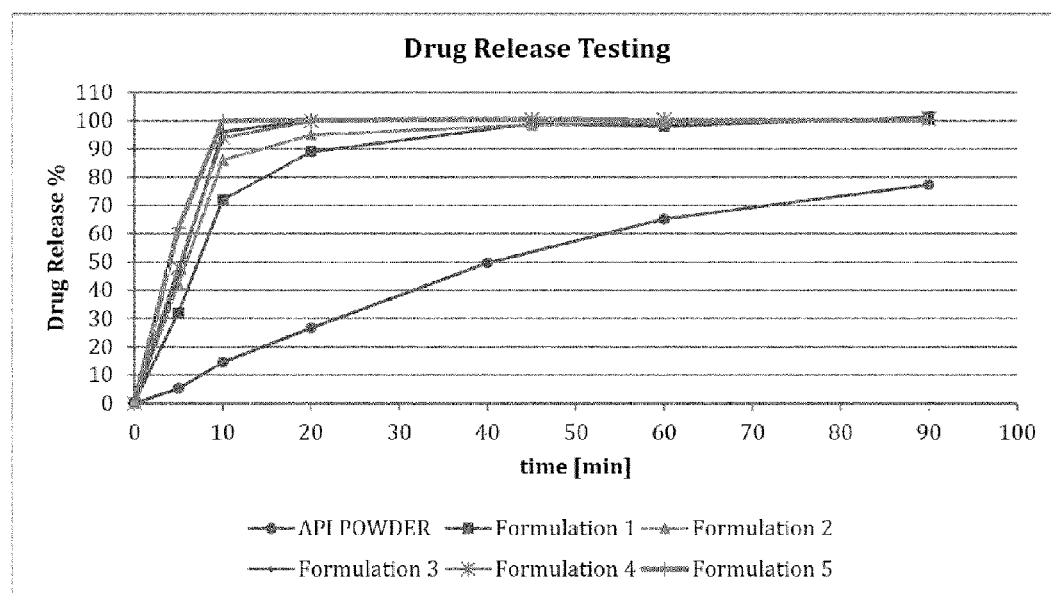
FIG. 3: Comparison of guanfacine hydrochloride release [%] of nanoparticle formulations and crude API (Phosphate Buffer pH 6.8+0.5% Tween 80)

FIG. 3 shows a comparison of drug release [%] of nanoparticle formulations of guanfacine HCl and the crude API (Phosphate Buffer pH 6.8+0.5% Tween 80).

Example 5

Different sustained release formulations were produced using the guanfacine HCl nanoparticles described in Formulation 5. This nanoparticle solution is mixed with PVP

TABLE 9

| Guanfacine HCl nanoparticle formulations | | | | | |
|---|---|---|---|---|---|
| | Formulation 1 | Formulation 2 | Formulation 3 | Formulation 4 | Formulation 5 |
| Solvent System | 6 mg/mL guanfacine HCl + 0.4 mg/mL Pluronic F68 in MeOH | 20 mg/mL guanfacine HCl + 40 mg/mL PVP K25 in 5 wt % citric acid | 12.5 mg/mL guanfacine HCl eq. complex in EtOH | 30 mg/mL guanfacine HCl eq. complex in EtOH | 90 mg/mL guanfacine HCl eq. complex in acetone |
| Non-Solvent System | 2 mg/mL PVP K25 in 0.1N KOH | 6 mg/mL SDS in 5 wt % citric acid | 2 wt % citric acid | pH 2.1 formic acid | pH 2.1 formic acid |
| Solvent/Non-Solvent Ratio | 1:1 (50 mL/min:50 mL/min) | 1:1 (50 mL/min:50 mL/min) | 1:1 (50 mL/min:50 mL/min) | 0.75:1 (37.5 mL/min:50 mL/min) | 1:2 (25 mL/min:50 mL/min) |
| Temperature [° C.] | 35.0 | 35.0 | 35.0 | 35.0 | 43.5 |
| Pressure [bar] | 0.2 | 0.2 | 0.2 | 0.2 | 1.95 |
| Additional processing | Filtration and drying | n.a. | n.a | n.a | n.a |

Formulation 1 and 2 were manufactured by using one step processes, whereas formulation 3, formulation 4 and formulation 5 required two steps for manufacturing.

K12 solution in water and granulated onto either ethyl cellulose, avicel, mannitol and HPMC or ethyl cellulose, avicel and mannitol or only avicel and mannitol.

TABLE 10

| Summarized oral 1 mg formulations prepared during the development (F1-F8) | | | | | | | | |
|---|---|---|---|---|---|---|---|---|
| | Amount in one tablet [mg] | | | | | | | |
| Ingredient | F1 | F2 | F3 | F4 | F5 | F6 | F7 | F8 |
| Granulation | | | | | | | | |
| G.HCl | 1.00 | 1.00 | 1.00 | 1.00 | 1.00 | 1.00 | 1.00 | 1.00 |
| SDS | 1.00 | 1.00 | 1.00 | 1.00 | 1.00 | 1.00 | 1.00 | 1.00 |
| Citric acid | 2.00 | 2.00 | 2.00 | 2.00 | 2.00 | 2.00 | 2.00 | 2.00 |
| EC | 45.00 | 30.00 | 30.00 | 25.00 | 20.00 | 12.00 | 12.00 | 12.00 |
| PVP K12 | 2.00 | 2.00 | 2.00 | 2.00 | 2.00 | 2.00 | 2.00 | 2.00 |
| Avicel | 54.00 | 69.00 | 69.00 | 74.80 | 79.80 | 74.80 | 74.80 | 30.00 |
| Mannitol | 45.00 | 45.00 | 45.00 | 45.00 | 45.00 | 45.00 | 45.00 | 60.00 |
| HPMC | — | — | — | — | — | 13.00 | 13.90 | 41.90 |
| After granulation | | | | | | | | |
| Mg stearate | 0.30 | 0.30 | 0.30 | 0.30 | 0.30 | 0.30 | 0.30 | 0.30 |
| Final amount | 150.3 | 150.3 | 150.00 | 151.10 | 151.10 | 151.10 | 152.00 | 150.20 |

TABLE 11

Summarized oral 1 mg formulations prepared during the development (F9-F16)

| Ingredient | Amount in one tablet [mg] | | | | | | | |
|---|---|---|---|---|---|---|---|---|
| | F9 | F10 | F11 | F12 | F13 | F14 | F15 | F16* |
| Granulation | | | | | | | | |
| G.HCl | 1.00 | 1.00 | 1.00 | 1.00 | 1.00 | 1.00 | 1.00 | 1.00 |
| SDS | 1.00 | 1.00 | 1.00 | 1.00 | 1.00 | 1.00 | 1.00 | 1.00 |
| Citric acid | 2.00 | 2.00 | 2.00 | 1.00 | 1.00 | — | — | — |
| EC | 41.90 | 5.00 | — | — | — | — | — | — |
| PVP K12 | 2.00 | 2.00 | 2.00 | 1.80 | — | 1.80 | 1.80 | 1.80 |
| Avicel | 30.00 | 30.00 | 30.00 | 73.90 | 75.70 | 75.70 | 75.70 | 75.70 |
| Mannitol | 60.00 | 60.00 | 60.00 | 41.00 | 41.00 | 41.00 | 40.00 | 40.00 |
| HPMC | 12.00 | — | — | — | — | — | — | — |
| After granulation | | | | | | | | |
| HPMC | — | 48.90 | 53.90 | 30.00 | 30.00 | 30.00 | 30.00 | 30.00 |
| Mg stearate | 0.30 | 0.30 | 0.30 | 0.30 | 0.30 | 0.30 | 0.75 | 0.75 |
| Aerosil 200 | — | — | — | — | — | — | 0.75 | 0.75 |
| Final amount | 150.20 | 150.20 | 150.20 | 150.00 | 150.00 | 150.80 | 151.00 | 151.00 |

*without nanoparticles, SDS is added in granulation

TABLE 12

Summarized oral 1 mg formulations prepared during the development (F17-F24)

| Ingredient | Amount in one tablet [mg] | | | | | | | |
|---|---|---|---|---|---|---|---|---|
| | F17 | F18* | F19 | F20 | F21 | F22 | F23* | F24 |
| Granulation | | | | | | | | |
| G.HCl | 1.00 | 1.00 | 1.00 | 1.00 | 1.00 | 1.00 | 1.00 | 1.00 |
| SDS | 1.00 | 1.00 | 1.00 | 1.00 | 1.00 | 1.00 | 1.00 | 1.00 |
| Citric acid | — | — | — | — | — | — | — | — |
| EC | — | — | — | — | — | — | — | — |
| PVP K12 | 1.80 | 1.80 | 1.80 | 1.80 | 1.80 | 1.80 | 1.80 | 1.80 |
| Avicel | 75.70 | 75.70 | 75.70 | 75.70 | 75.70 | 75.70 | 75.70 | 75.70 |
| Mannitol | 42.00 | 41.00 | 42.00 | 42.00 | 41.00 | 41.00 | 41.00 | 41.00 |
| HPMC | — | — | — | 1.00 | 1.00 | 1.00 | 1.00 | 1.00 |
| After granulation | | | | | | | | |
| HPMC | 30.00 | 30.00 | 30.00 | 30.00 | 31.00 | 32.00 | 33.00 | 36.00 |
| Mg stearate | 0.30 | 0.30 | 0.75 | 0.75 | 0.75 | 0.75 | 0.75 | 0.75 |
| Aerosil 200 | — | — | 0.75 | 0.75 | 0.75 | 0.75 | 0.75 | 0.75 |
| Final amount | 151.80 | 150.80 | 153.0 | 153.00 | 153.00 | 154.00 | 155.00 | 158.00 |

*without nanoparticles, SDS is added in granulation

TABLE 13

Summarized oral 1 mg formulations prepared during the development (F25-F32)

| Ingredient | Amount in one tablet [mg] | | | | | | | |
|---|---|---|---|---|---|---|---|---|
| | F25 | F26 | F27 | F28 | F29* | F30* | F31* | F32* |
| Granulation | | | | | | | | |
| G.HCl | 1.15 | 1.15 | 1.15 | 1.15 | 1.15 | 1.15 | 1.15 | 1.15 |
| SDS | 1.15 | 1.15 | 1.15 | 1.15 | 1.15 | 1.15 | 1.15 | 1.15 |
| EC | — | — | — | — | — | — | — | — |
| PVP K12 | 1.80 | — | — | — | 3.60 | 3.60 | 3.60 | 3.60 |
| Avicel | — | 1.80 | 1.80 | 3.60 | — | — | — | — |
| Mannitol | 75.70 | 75.70 | 75.70 | 75.70 | 75.70 | 75.70 | 75.70 | 75.70 |
| HPMC | 41.00 | 41.00 | 41.00 | 41.00 | 46.90 | 41.90 | 46.90 | 46.90 |

TABLE 13-continued

Summarized oral 1 mg formulations prepared during the development (F25-F32)

| Ingredient | Amount in one tablet [mg] | | | | | | | |
|---|---|---|---|---|---|---|---|---|
| | F25 | F26 | F27 | F28 | F29* | F30* | F31* | F32* |
| After granulation | | | | | | | | |
| HPMC | 30.00 | 30.00 | 30.00 | 30.00 | 20.00 | 25.00 | 20.00 | 20.00 |
| Mg stearate | 0.75 | 0.75 | 0.75 | 0.75 | 0.75 | 0.75 | 0.75 | 0.75 |
| Aerosil 200 | 0.75 | 0.75 | 0.75 | 0.75 | 0.75 | 0.75 | 0.75 | 0.75 |
| PVP K90 | — | — | — | — | — | — | — | 1.80 |
| Final amount | 152.30 | 152.30 | 152.30 | 154.10 | 150.00 | 150.00 | 150.00 | 151.80 |

*PVP was added in granulation as powder

TABLE 14

Summarized oral 1 mg formulations prepared during the development (F33-F40)

| Ingredient | Amount in tablet [mg] | | | | | | | |
|---|---|---|---|---|---|---|---|---|
| | F33* | F34* | F35* | F36* | F37* | F38* | F39 | F40 |
| Granulation | | | | | | | | |
| G.HCl | 1.15 | 1.15 | 1.15 | 1.15 | 1.15 | 1.15 | 1.15 | 1.15 |
| SDS | 1.15 | 1.15 | 1.15 | 1.15 | 1.15 | 1.15 | 1.15 | 1.15 |
| EC | — | — | — | — | — | — | — | — |
| PVP K12 | — | — | — | — | — | — | 0.84 | 0.84 |
| PVP K25 | 7.50 | 7.50 | 7.50 + 1.80** | 7.50 | 7.50 | 3.60 | — | — |
| Avicel | 75.70 | 75.70 | 75.36 | 75.36 | 75.70 | 75.70 | 75.40 | 85.40 |
| Mannitol | 42.00 | 41.00 | 43.00 | 43.00 | 43.00 | 46.90 | 41.00 | 41.00 |
| After granulation | | | | | | | | |
| HPMC | 20.00 | 20.00 | 20.00 | 20.00 | 20.00 | 20.00 | 20.00 | 20.00 |
| Mg stearate | 0.75 | 0.75 | 0.75 | 0.75 | 0.75 | 0.75 | 0.75 | 0.75 |
| Aerosil 200 | 0.75 | 0.75 | 0.75 | 0.75 | 0.75 | 0.75 | 0.75 | 0.75 |
| Final amount | 149.00 | 148.00 | 150.46 | 149.66 | 150.00 | 150.00 | 141.04 | 151.04 |

*PVP was added in granulation as powder
**PVP was added as 5% solution in water

TABLE 15

Summarized oral 1 mg formulations prepared during the development (F41-F42)

| Ingredient | Amount in one tablet [mg] | |
|---|---|---|
| | F41 | F42 |
| Granulation | | |
| G.HCl | 1.15 | 1.15 |
| SDS | 1.15 | 1.15 |
| EC | — | — |
| PVPK12 | 0.84 | 0.84 |
| Avicel | 75.70 | 72.36 |
| Mannitol | 41.00 | 41.00 |
| After granulation | | |
| HPMC | 32.00 | 32.00 |
| Mg stearate | 0.75 | 0.75 |
| Aerosil 200 | 0.75 | 0.75 |
| Final amount | 153.34 | 150.00 |

TABLE 16

Final receipt for 1 and 2 mg tablets

| Substance | m/500 gram [g] |
|---|---|
| G.HCl | 3.75 |
| SDS | 3.75 |
| PVPK12 | 2.74 |
| Avicel | 246.84 |
| Mannitol | 133.69 |
| After granulation | |
| HPMC | 104.34 |
| Mg Stearate | 2.45 |
| Aerosil 200 | 2.45 |
| Final Amount | 500 |

TABLE 17

Final receipt for 3 and 4 mg tablets

| Substance | m/500 gram [g] |
|---|---|
| G.HCl | 8.63 |
| SDS | 8.63 |
| PVPK12 | 2.10 |

TABLE 17-continued

Final receipt for 3 and 4 mg tablets

| Substance | m/500 gram [g] |
|---|---|
| Avicel | 237.98 |
| Mannitol | 157.68 |
| After granulation | |
| HPMC | 80 |
| Mg Stearate | 2.5 |
| Aerosil 200 | 2.5 |
| Final Amount | 500 |

Example 6

Figure 15:
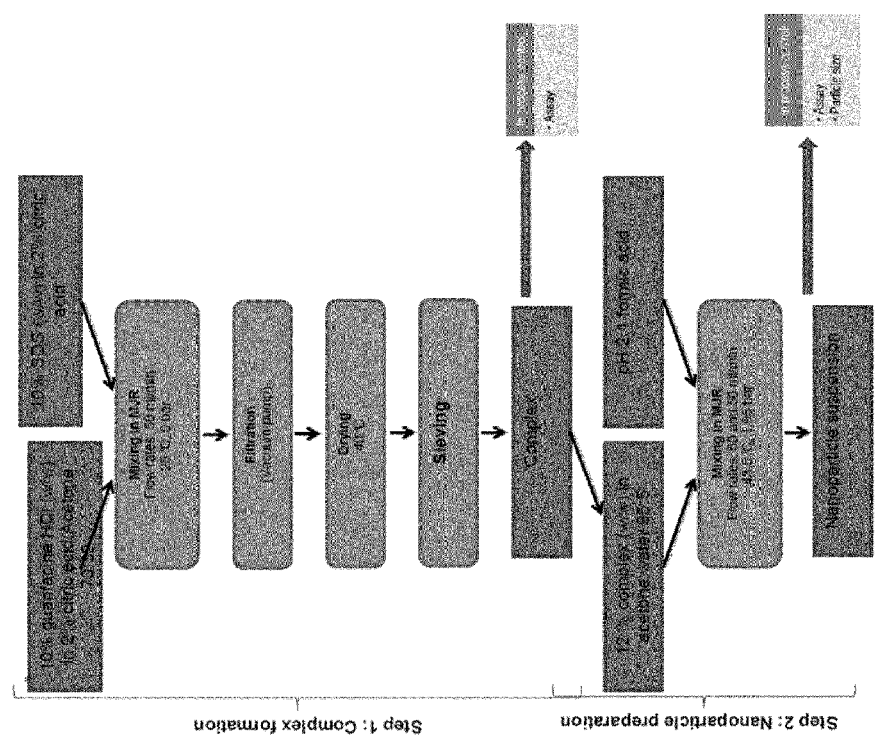
FIGS. 15 and 16: Flow charts of the production process of Example 6.
Figure 16:
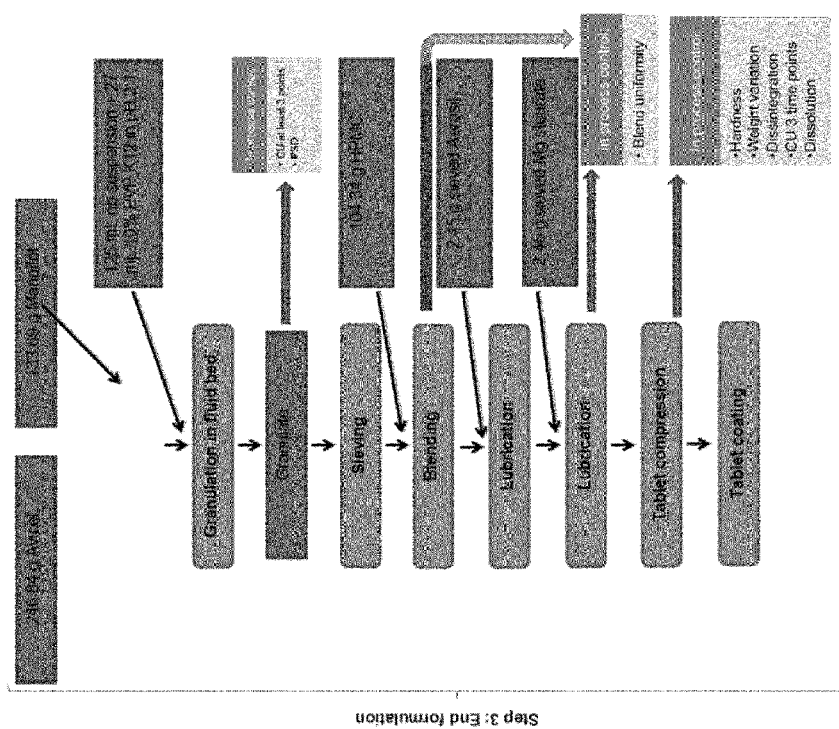

Production process formulation 1, 2, 3 and 4 mg tablets. It is referred to the flow charts shown in FIGS. 15 and 16.

Example 7

Dissolution studies were conducted in two different pH's to show the pH independent release of guanfacine HCl formulated as nanoparticular sustained release formulation.

TABLE 18

Dissolution testing parameters

| System | Erweka DT-6 |
|---|---|
| USP Apparatus | II (Paddle) |
| Speed [rpm] | 50 |
| Medium | Buffer 0.1N HCL pH 1.2 or Phosphate Buffer pH 6.8 |
| Volume [mL] | 500 |
| Medium Temperature [° C.] | 37.0 ± 0.5 |
| Sampling Times [h] | adapted to buffer used, up to 14 h |

After reaching a temperature of 37° C. degrees, the test tablet was placed into each vessel which was performed by 30 seconds difference between each vessel. This time interval difference was taken into consideration during whole sampling. Temperature in the reference vessel was controlled and documented for each sampling time point. All dissolution determinations were carried out with sinkers. 5 mL of sample was withdrawn from each vessel for each sampling point. Samples taken were filtrated using 1.0 µm glass syringe filters. The first 3 ml is transferred back into the vessel, while rest of the samples was transferred to a vial. Samples were analyzed by employing validated HPLC method.

Figure 4:
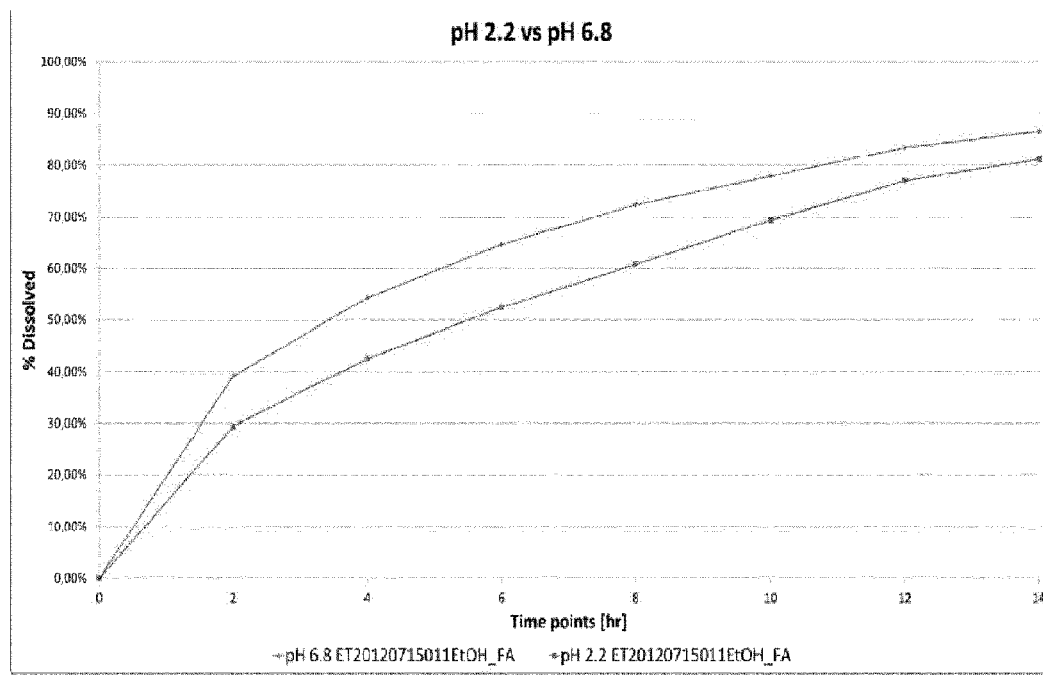
FIG. 4: Mean dissolution rates of guanfacine hydrochloride from the sustained release formulations in buffer at pH 2.2 and pH 6.8. The values shown are mean values from experiments performed in parallel (n=6).

FIG. 4 shows the mean dissolution rates of guanfacine hydrochloride from the sustained release formulations in buffer at pH 2.2 and pH 6.8. The values shown are mean values from experiments performed in parallel (n=6). Dissolution data show that the pH dependent solubility of the compound was overcome by sustained release formulation of Guanfacine nanoparticles as dissolution is even more pronounced at pH 6.8 than in pH 2.2.

Example 8

Formulations shown in Table 19 were developed in order to increase oral bioavailability of guanfacine HCl formulated as nanoparticular sustained release formulation in comparison to the marketed reference medication. Three formulations with reduced doses of guanfacine HCl were formulated: 3.5, 3.0 and 2.5 mg.

TABLE 19

Final receipt for superbioavailable tablets T2

| | Amount in one tablet [mg] | | |
|---|---|---|---|
| Ingredient | F1 (2.5 mg) | F2 (3.0 mg) | F3 (3.5 mg) |
| Granulation | | | |
| G.HCl | 2.85 | 3.42 | 3.99 |
| SDS | 2.85 | 3.42 | 3.99 |
| Citric acid | 10 | 10 | 10 |
| PVP K12 | 0.84 | 0.84 | 0.84 |
| Avicel | 95.19 | 95.19 | 95.19 |
| Mannitol | 58.27 | 57.13 | 55.99 |
| After granulation | | | |
| HPMC | 28 | 28 | 28 |
| Mg stearate | 1 | 1 | 1 |
| Aerosil 200 | 1 | 1 | 1 |
| Final amount | 200 | 200 | 200 |

Example 9

Figure 17:
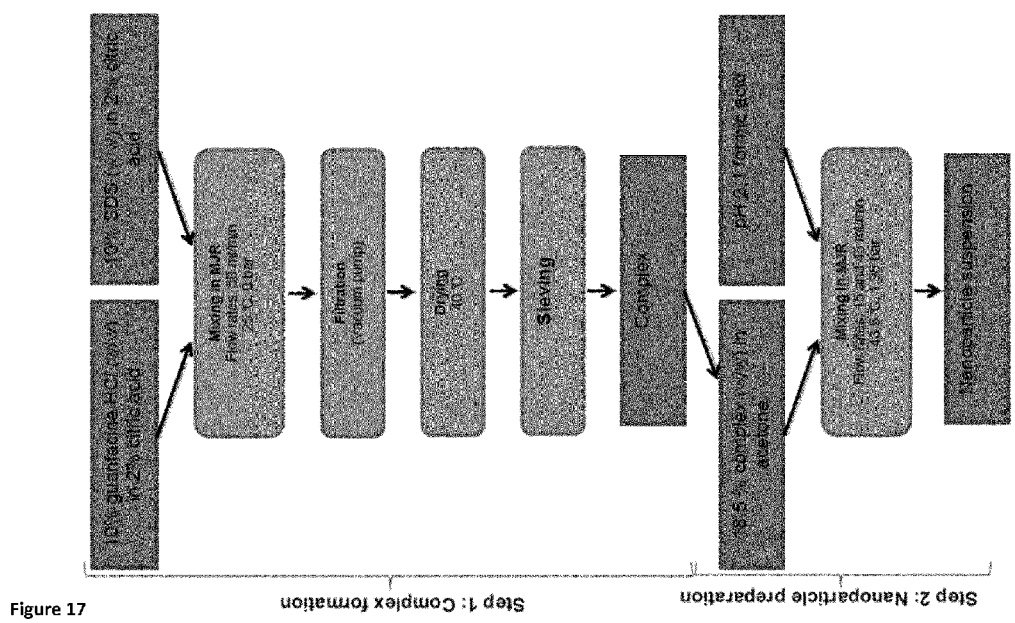
FIGS. 17 and 18: Flow charts of the production process of Example 9.
Figure 18:
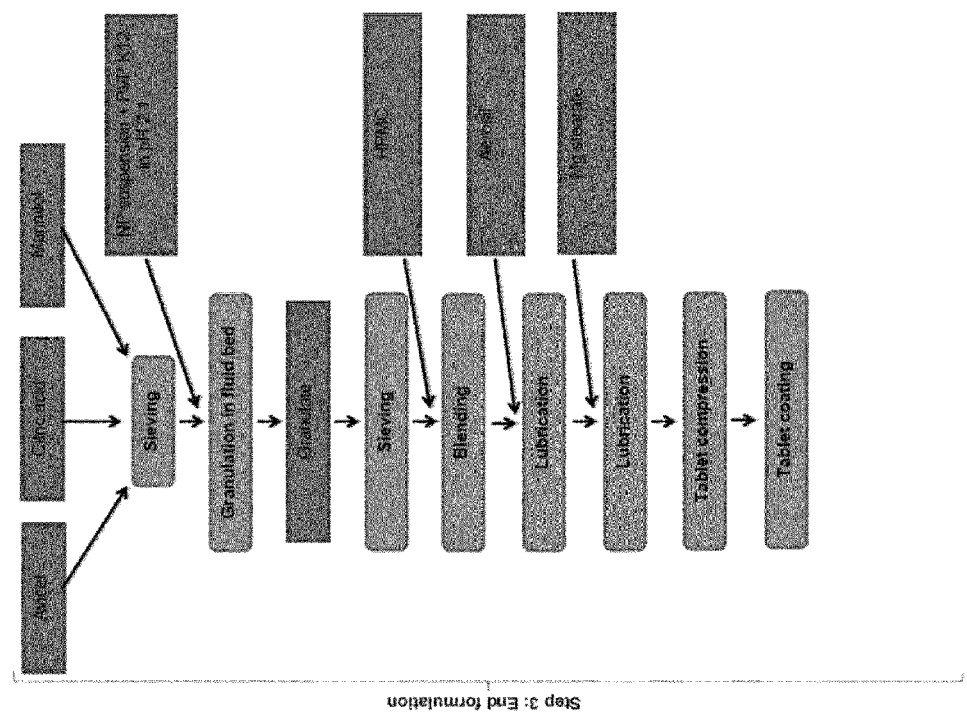

Process flow chart for superbioavailable tablets. It is referred to the flow charts shown in FIGS. 17 and 18.

Example 10

Dissolution properties of superbioavailable tablet formulations T2 in pH 2.2 and pH 6.8.

TABLE 20

Dissolution testing parameters

| System | Erweka DT-6 |
|---|---|
| USP Apparatus | II (Paddle) |
| Speed [rpm] | 50 |
| Medium | pH 2.2 buffer or pH 6.8 buffer |
| Volume [mL] | 500 |
| Medium Temperature [° C.] | 37.0 ± 0.5 |
| Sampling Times [h] | Buffer dependent, up to 22 hours |

Figure 5:
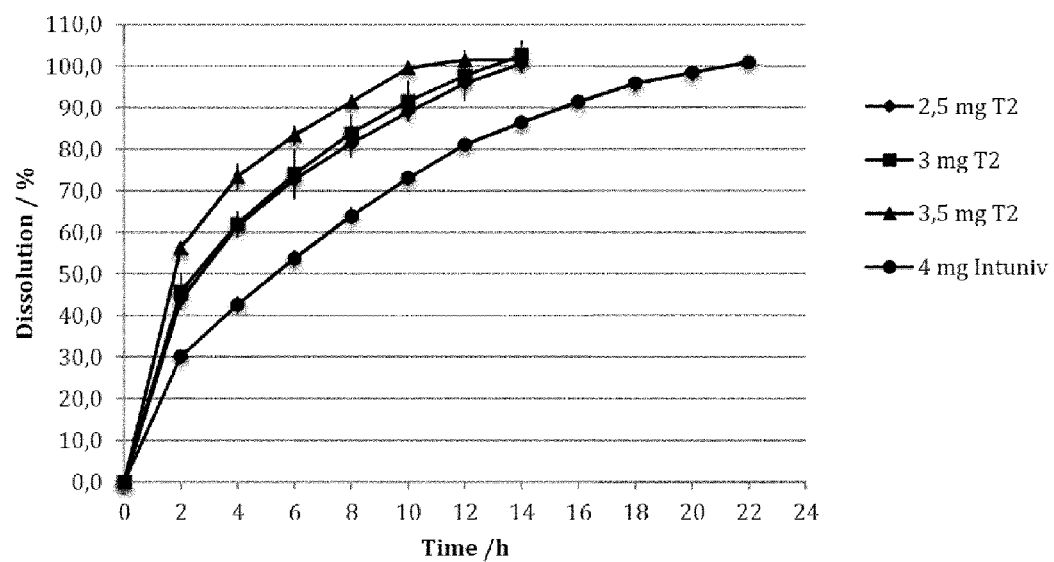
FIG. 5: Mean dissolution rates of guanfacine hydrochloride from the sustained release formulations T2 and the reference in buffer at pH 2.2 The values shown are mean values from experiments performed in parallel (n=6).
Figure 6:
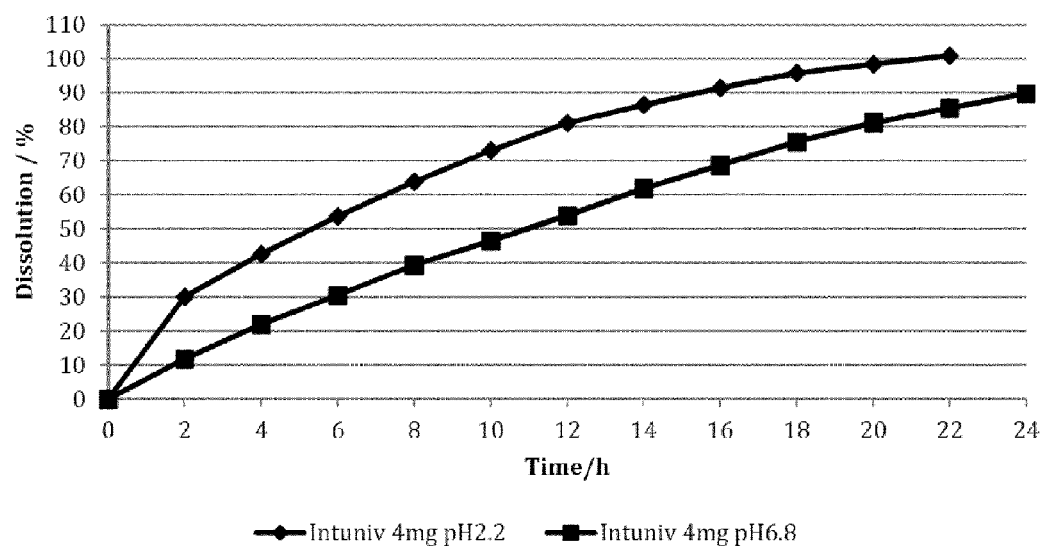
FIG. 6: Mean dissolution rates of Intuniv® 4 mg in buffer pH 2.2 and pH 6.8. The values shown are mean values from experiments performed in parallel (n=3).
Figure 7:
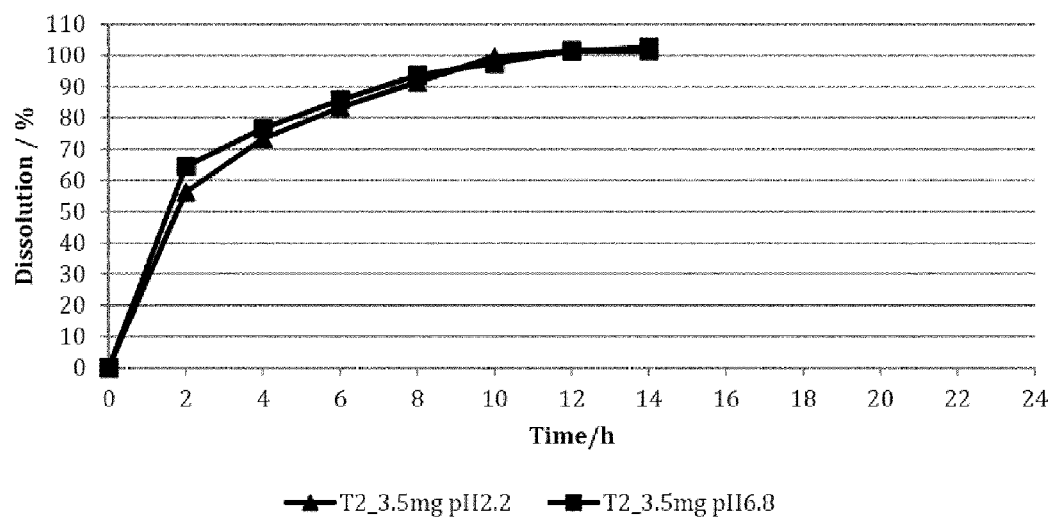
FIG. 7: Mean dissolution rates of T2_3.5 mg in buffer pH 2.2 and pH 6.8. The values shown are mean values from experiments performed in parallel (n=3).
Figure 8:
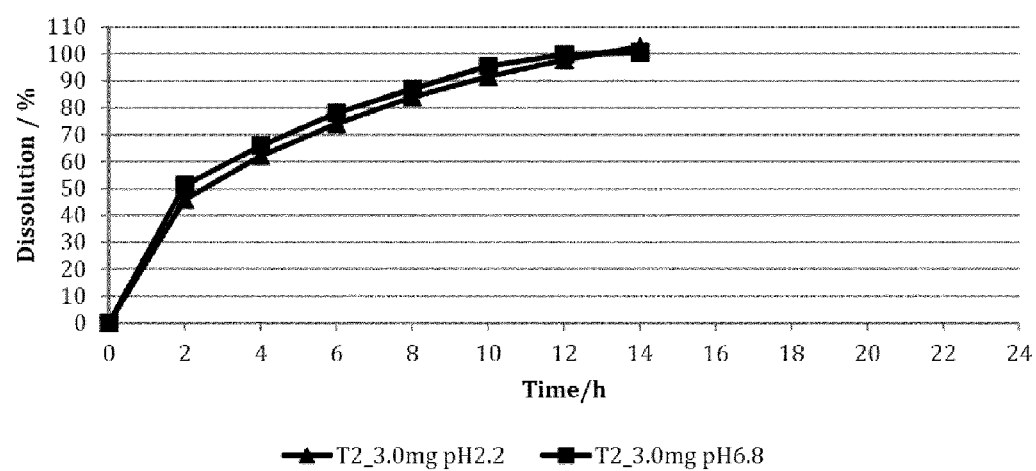
FIG. 8: Mean dissolution rates of T2_3.0 mg in buffer pH 2.2 and pH 6.8. The values shown are mean values from experiments performed in parallel (n=3).
Figure 9:
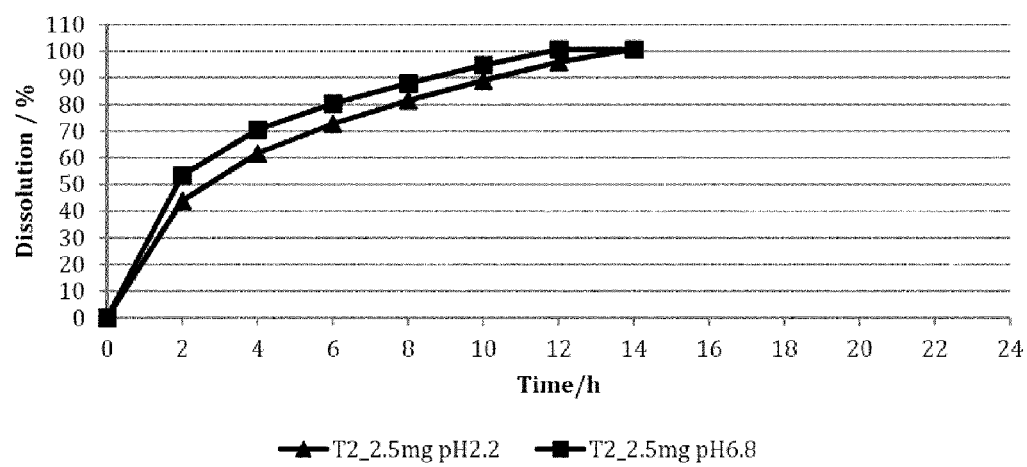
FIG. 9: Mean dissolution rates of T2_2.5 mg in buffer pH 2.2 and pH 6.8. The values shown are mean values from experiments performed in parallel (n=3).

After reaching a temperature of 37° C. degrees, test tablet was placed into each vessel which was performed by 30 seconds difference between each vessel. This time interval difference was taken into consideration during whole sampling. Temperature in the reference vessel was controlled and documented for each sampling time point. All dissolution determinations were carried out with sinkers. 5 mL of sample was withdrawn from each vessel for each sampling point. Samples taken were filtrated using 1.0 µm glass syringe filters. The first 3 ml is transferred back into the vessel, while rest of the samples was transferred to a vial. Samples were analyzed by employing validated HPLC method. As shown in FIG. 5 T2 formulations of guanfacine HCl showed an increased dissolution rate compared to the reference Intuniv® at pH 2.2. FIG. 6 shows the pH dependent release of the reference formulation Intuniv® as described before. FIG. 7, FIG. 8 and FIG. 9 show that with the developed T2 formulations pH dependency of in vitro release could be abolished.

FIG. 5 shows the mean dissolution rates of guanfacine hydrochloride from the sustained release formulations T2 and the reference in buffer at pH 2.2 The values shown are mean values from experiments performed in parallel (n=6).

FIG. 6 shows the mean dissolution rates of Intuniv® 4 mg in buffer pH 2.2 and pH 6.8. The values shown are mean values from experiments performed in parallel (n=3).

FIG. 7 shows the mean dissolution rates of T2_3.5 mg in buffer pH 2.2 and pH 6.8. The values shown are mean values from experiments performed in parallel (n=3).

FIG. 8 shows the mean dissolution rates of T2_3.0 mg in buffer pH 2.2 and pH 6.8. The values shown are mean values from experiments performed in parallel (n=3).

FIG. 9 illustrates the mean dissolution rates of T2_2.5 mg in buffer pH 2.2 and pH 6.8. The values shown are mean values from experiments performed in parallel (n=3).

Example 11

Preclinical Data

Taking the characteristics of nanoparticles and the in vitro dissolution results into consideration, one supposed that oral bioavailability of the API could be increased using an improved extended release formulation of guanfacine HCl (T2).

In order to show proof of principle 18 healthy male dogs were treated with the reference medication (4 mg) and test formulations T2 in the reduced dose strengths 3.5 mg, 3.0 mg and 2.5 mg with n=6 per group in parallel design (oral application, single dose, fasted), corresponding to a dose reduction of guanfacine HCl of 12.5%, 25% and 37.5%. Plasma samples were taken at the time points 0, 1, 2, 3, 4, 5, 6, 7, 8, 10, 12, 24, 48 and 72 hours. Guanfacine HCl concentration in plasma samples was quantified by applying a validated HPLCMS/MS method. In order to handle high variability and limited group size, median PK parameters were used for interpretation of results. Use of median calculations is an established mathematical method to strengthen the informative value of data demonstrating small sample size and/or high data variability.

Figure 10:
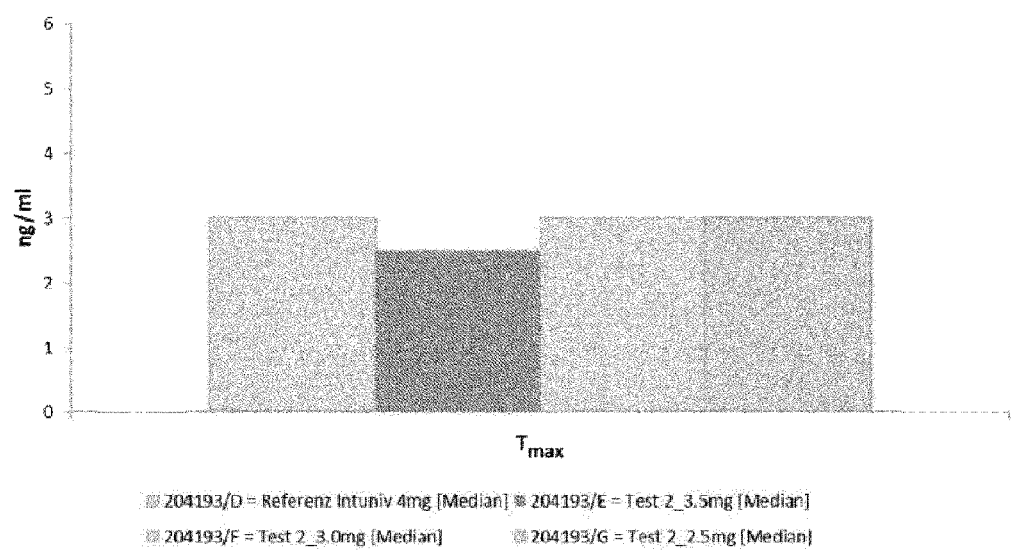
FIG. 10 depicts the median $t_{max}$ values for reference medication 4 mg and test formulations T2 3.5 mg, 3 mg and 2.5 mg.
Figure 11:
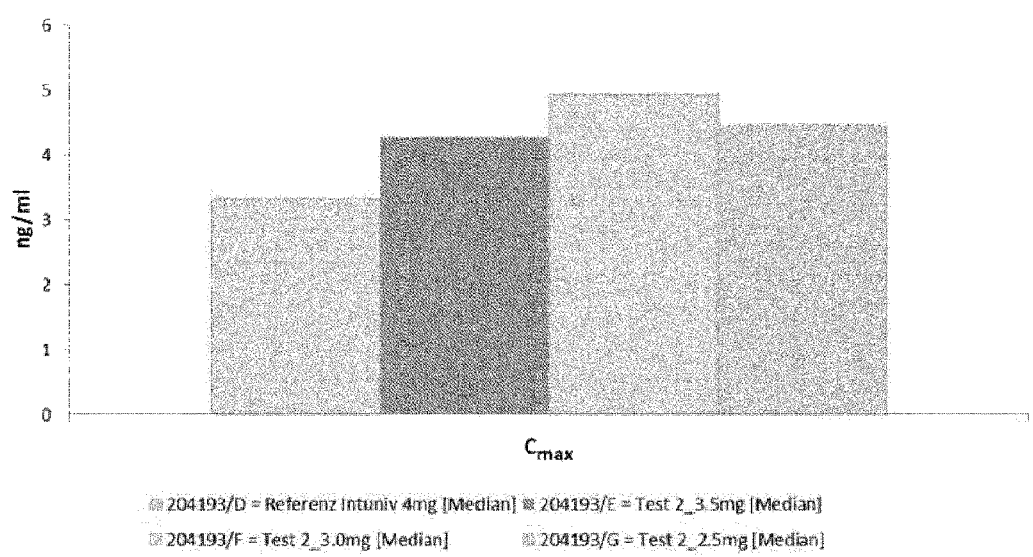
FIG. 11 illustrates the median $c_{max}$ values for reference medication 4 mg and test formulations T2 3.5 mg, 3 mg and 2.5 mg.
Figure 12:
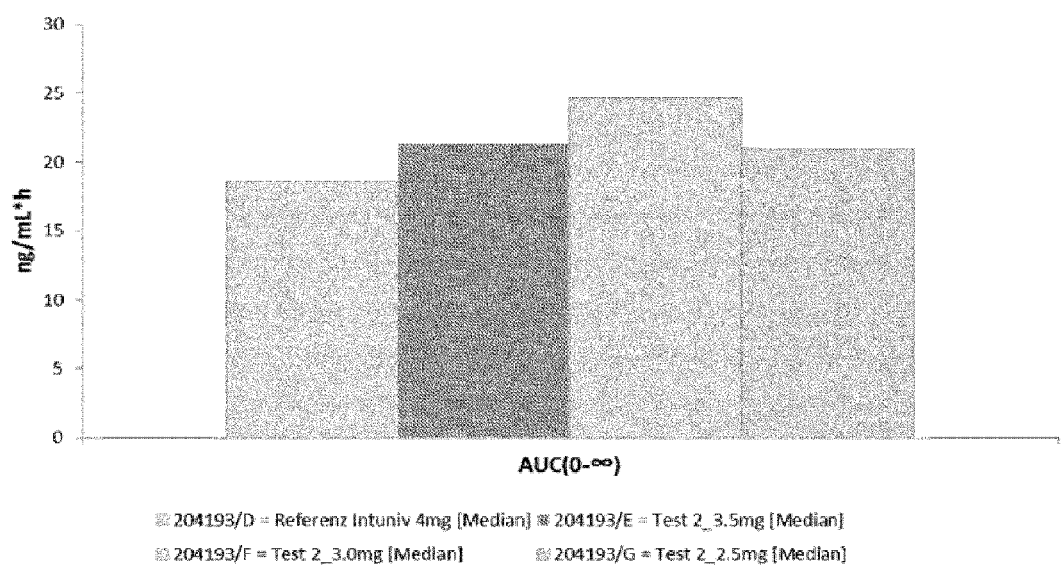
FIG. 12 shows the median AUC (0-∞) values for reference medication 4 mg and test formulations T2 3.5 mg, 3 mg and 2.5 mg.

The $t_{max}$ values of the test formulations showed similar values compared to the reference group (FIG. 10). However, the comparison of $c_{max}$ and AUC values indicates that the effective API dose of the superbioavailable formulations T2 has to be further reduced as median $c_{max}$ and AUC values of the three tested dose strengths (3.5 mg, 3.0 mg and 2.5 mg) lie clearly above the plasma levels found for the reference Intuniv® 4 mg, as shown in FIG. 11 and FIG. 12, leading to a relative oral bioavailability of 130%, 166% respectively 146% in comparison to the reference (Table 21 and FIG. 13). Comparison of median PK profiles normalized to the group-specific median $c_{max}$ of the reference formulation and the test formulation show comparable plasma concentration vs. time profiles for the test formulations T2_3.0 mg and T2_2.5 mg to the originator profile indicating a comparable release of the test formulation in vivo (FIG. 14).

The gathered in vivo data strengthen the working hypothesis: Oral bioavailability of guanfacine HCl formulated as nanoparticular extended release product can be increased to more than 44% absolute bioavailability allowing for a reduction of effective API dose by more than 37.5%.

FIG. 10 depicts the median $t_{max}$ values for reference medication 4 mg and test formulations T2 3.5 mg, 3 mg and 2.5 mg.

FIG. 11 illustrates the median $c_{max}$ values for reference medication 4 mg and test formulations T2 3.5 mg, 3 mg and 2.5 mg.

FIG. 12 shows the median AUC (0-∞) values for reference medication 4 mg and test formulations T2 3.5 mg, 3 mg and 2.5 mg.

Figure 13:
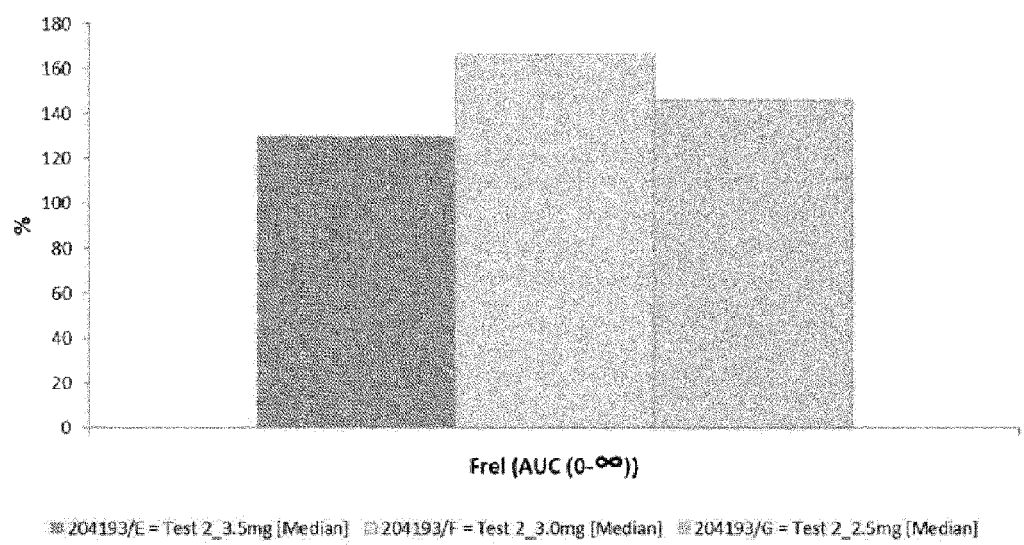
FIG. 13 shows the relative bioavailability of test formulations T2 3.5 mg, 3 mg and 2.5 mg in comparison to the reference medication 4 mg.
Figure 14:
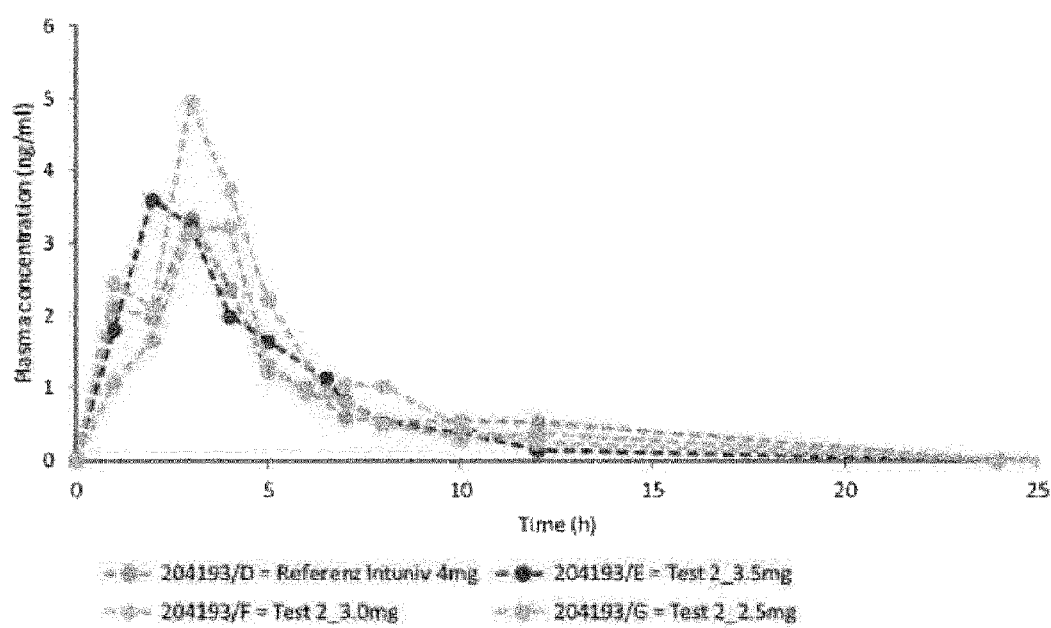
FIG. 14: Superimposed median PK profiles normalized to the group specific $c_{max}$.

FIG. 13 shows the relative bioavailability of test formulations T2 3.5 mg, 3 mg and 2.5 mg in comparison to the reference medication 4 mg.

FIG. 14: Superimposed median PK profiles normalized to the group specific $c_{max}$.

TABLE 21

Median PK parameters

| Animal Species | Dog | | | |
| --- | --- | --- | --- | --- |
| Strain | Beagle | | | |
| Gender | male | | | |
| Test item | Reference | T2 | T2 | T2 |
| Dose route | po | po | po | po |
| PK analysis software | Kinetica 5.0 | Kinetica 5.0 | Kinetica 5.0 | Kinetica 5.0 |
| Dose (mg/animal) | 4.0 | 3.5 | 3.0 | 2.5 |
| | Median | Median | Median | Median |
| Dose (mg/kg) | 0.37 | 0.34 | 0.29 | 0.25 |
| Cmax (ng/ml) | 3.35 | 4.28 | 4.95 | 4.47 |
| tmax (h) | 3.0 | 2.5 | 3.0 | 3.0 |
| Cz (ng/ml) | 0.50 | 0.28 | 0.34 | 0.36 |
| tz (h) | 12.0 | 11.0 | 12.0 | 12.0 |
| AUC(0-8 h) (ng*h/ml) | 13.6 | 18.6 | 20.0 | 17.9 |
| AUC(0-10 h) (ng*h/ml) | 14.5 | 20.3 | 22.2 | 21.6 |
| AUC(0-tz) (ng*h/ml) | 14.8 | 20.2 | 23.4 | 17.9 |
| AUC(0-inf) (ng*h/ml) | 18.6 | 21.3 | 24.6 | 21.0 |
| % AUCextra | 12.8 | 3.7 | 2.5 | 4.5 |
| t½ | 3.2 | 1.8 | 1.5 | 1.8 |
| CL/F (l/kg) (not normalized to F) | 16.8 | 15.4 | 11.9 | 12.6 |
| Vz/F (l/(h*kg)) (not normalized to F) | 68.7 | 43.0 | 26.1 | 30.0 |
| $F_{rel}$ ($C_{max}$) (%) | | 141 | 201 | 166 |
| $F_{rel}$ ($T_{max}$) (%) | | 83 | 100 | 100 |
| $F_{rel}$ (AUC (0-8 h)) (%) | | 148 | 179 | 193 |
| $F_{rel}$ (AUC (0-10 h)) (%) | | 162 | 188 | 143 |
| $F_{rel}$ (AUC (0-tz)) (%) | | 155 | 193 | 177 |
| $F_{rel}$ (AUC (0-inf)) (%) | | 130 | 166 | 146 |

Example 12

Dose Dumping Studies

Dose dumping effect in the presence of alcohol was evaluated with the following formulations.

TABLE 22

Formulation compositions for the 4 mg tablets produced for dose dumping studies

| | Formulation receipt D1 [mg/tab] | Formulation receipt D2 [mg/tab] |
| --- | --- | --- |
| Guanfacine HCl | 4.60 | 4.60 |
| Sodium Dodecyl Sulfate | 4.60 | 4.60 |
| PVP K30 | 5.59 | 5.59 |
| Microcrystalline Cellulose | 185.45 | 175.69 |
| Lactose | 9.76 | 19.52 |
| HPMC | 48.00 | 48.00 |
| Compritol | 8.00 | 8.00 |
| SUM | 266.00 | 266.00 |

Nanoparticles were prepared as described in example 9 and granulated on microcrystalline cellulose and lactose mixture. After drying and sieving of the granules, the powder was further mixed with HPMC and compritol.

Dissolution studies as described in Example 10 were conducted using HCl buffer pH 2.2, water and 40% EtOH

TABLE 23

Results of dissolution studies with
HCl buffer pH 2.2, water and 40% EtOH

| Formulation receipt | Dissolution medium | 0 | 1 | 2 | 3 | 4 | 5 | 6 |
|---|---|---|---|---|---|---|---|---|
| D1 | pH 2.2 HCl Buffer | 0 | 31.7 | 42.3 | 50.1 | 56.9 | 61.2 | 65.8 |
| D1 | water | 0 | 28.5 | 36.8 | 43.2 | 48.6 | 53.2 | 56.9 |
| D1 | 40% EtOH | 0 | 24.8 | 33.3 | 41.7 | 47.3 | 53.1 | 58.1 |
| D2 | pH 2.2 HCl Buffer | 0 | 31.3 | 41.0 | 48.5 | 54.5 | 59.3 | 63.8 |
| D2 | water | 0 | 28.0 | 35.3 | 41.1 | 46.3 | 50.5 | 54.5 |
| D2 | 40% EtOH | 0 | 24.7 | 34.9 | 42.5 | 49.2 | 55.3 | 60.4 |

As shown in Table 21 there was no dose dumping in the presence of EtOH for formulations D1 and D2.

The invention claimed is:

1. A pharmaceutical composition comprising guanfacine or a salt thereof and at least one non pH-dependent sustained release agent, wherein the guanfacine or the salt thereof is incorporated in nanoparticles having a size of from 70 to 1,000 nm and having a polydispersity index of ≤0.5, and further wherein the guanfacine or the salt thereof is complexed with sodium dodecylsulfate (SDS).

2. The pharmaceutical composition of claim 1, wherein the size of the nanoparticles is 100-500 nm.

3. The pharmaceutical composition of claim 1, wherein the polydispersity index is below 0.2.

4. The pharmaceutical composition of claim 1, wherein the guanfacine salt is guanfacine HCl.

5. The pharmaceutical composition of claim 1, wherein the at least one non pH-dependent sustained release agent is selected from the group consisting of a carbohydrate gum, a polyuronic acid salt, a cellulose ether, and an acrylic polymer.

6. A method of producing nanoparticles containing guanfacine or a salt thereof, the method comprising:
   a) providing a fluid mixture of guanfacine or a salt thereof complexed with sodium dodecylsulfate (SDS) with a solvent; and a fluid non-solvent;
   b) precipitating nanoparticles containing the guanfacine or the salt thereof by colliding fluid streams of the fluid mixture and the non-solvent; and
   c) isolating the nanoparticles containing the guanfacine or the salt thereof as a nanoparticle suspension.

7. The method of claim 6, wherein the solvent is selected from the group consisting of methanol, ethanol, t-butanol, acetone, and mixtures thereof.

8. The method of claim 6, wherein the solvent is an acidic aqueous solvent.

9. The method of claim 6, wherein the non-solvent is an aqueous alkaline solvent.

10. The method of claim 6, wherein the non-solvent is an acidic aqueous solvent.

11. The method of claim 6, wherein the fluid mixture of guanfacine or the salt thereof complexed with SDS with the solvent and/or the non-solvent further comprises one or more additional active pharmaceutical ingredients (API's) and/or pharmaceutically acceptable auxiliaries.

12. The method of claim 6, wherein the fluid streams are collided with a velocity of more than 1 m/sec.

13. The method of claim 6, where the complex is formed by precipitation of the complex from a solution of guanfacine or a salt thereof in acidic media and an acidic solution.

14. The method of claim 13, wherein the formed complex is dissolved in an organic solvent and is precipitated against an acidic solution as a non-solvent to provide nanoparticles.

15. The method of claim 13, wherein the acidic media/solution is a citric acid, acetic acid, formic acid or hydrochloric acid media/solution.

16. The method of claim 6, wherein the volume ratio of the liquids of the solvent and non-solvent is between 1:1 and 1:2.

17. The method of claim 6, further comprising subjecting the nanoparticle suspension to a granulation step with a suitable excipient.

18. Nanoparticles obtained by the method of claim 6.

19. A pharmaceutical composition comprising the nanoparticles of claim 18 and at least one pharmaceutically acceptable excipient.

20. The pharmaceutical composition of claim 5, wherein the at least one non pH-dependent sustained release agent is selected from the group consisting of xanthan gum, tragacanth gum, gum karaya, guar gum, acacia, gellan and locust bean gum, sodium alginate, potassium alginate, ammonium alginate, ethylcellulose, hydroxypropyl methylcellulose, hydroxypropyl cellulose, hydroxyethyl cellulose, an polyacrylic polymer, and a carboxy vinyl polymer.

21. The method of claim 8, wherein the acidic aqueous solvent, the non-solvent, or both are selected from the group consisting of citric acid, acetic acid, formic acid, and a hydrochloric acid solution.

22. The method of claim 21, wherein the acidic aqueous solvent, the non-solvent, or both is an aqueous citric acid solution.

23. The method of claim 9, wherein the aqueous alkaline solvent is selected from the group consisting of an aqueous NaOH solution and an aqueous KOH solution.

24. The method of claim 12, wherein the fluid streams are collided with a velocity of more than 50 m/sec.

25. The method of claim 13, where the complex is formed by precipitation of the complex from a solution of guanfacine or a salt thereof complexed with SDS in the acidic media and the acidic solution in the absence of stabilizing agents.

26. The method of claim 14, wherein the organic solvent is selected from the group consisting of methanol, ethanol, isopropanol, and acetone.

* * * * *